United States Patent [19]

McLaren et al.

[11] Patent Number: 5,925,374
[45] Date of Patent: Jul. 20, 1999

[54] ANTHELMINTIC PREPARATION

[75] Inventors: Donald George McLaren; Wayne Frederick Leech, both of Auckland, New Zealand

[73] Assignee: Bomac Laboratories Limited, Manukau City, New Zealand

[21] Appl. No.: 08/666,325

[22] PCT Filed: Mar. 2, 1995

[86] PCT No.: PCT/NZ95/00023

§ 371 Date: Sep. 27, 1996

§ 102(e) Date: Sep. 27, 1996

[87] PCT Pub. No.: WO95/23590

PCT Pub. Date: Sep. 8, 1995

[30] Foreign Application Priority Data

Mar. 3, 1994 [NZ] New Zealand ............................ 260018

[51] Int. Cl.$^6$ ...................................................... A61K 9/70
[52] U.S. Cl. .......................... 424/449; 514/393; 514/394; 514/395; 514/396
[58] Field of Search ............................. 424/449; 514/393, 514/394, 395, 396

[56] References Cited

U.S. PATENT DOCUMENTS

| | | | |
|---|---|---|---|
| 3,852,336 | 12/1974 | Harfenist | 260/485 J |
| 4,018,932 | 4/1977 | Spicer et al. | 424/270 |
| 4,145,433 | 3/1979 | Haugwitz et al. | 424/273 B |
| 4,672,072 | 6/1987 | Hackney et al. | 514/368 |
| 5,169,846 | 12/1992 | Crooks | 514/224.8 |
| 5,324,521 | 6/1994 | Gertner et al. | 424/449 |

FOREIGN PATENT DOCUMENTS

| | | |
|---|---|---|
| A-27505/88 | 7/1989 | Australia . |
| A-10277/92 | 8/1992 | Australia . |
| A-12978/92 | 10/1992 | Australia . |
| 39352/93 | 9/1993 | Australia . |
| 0 137 627 A2 | 4/1985 | European Pat. Off. . |
| 186378 | 12/1980 | New Zealand . |
| 223200 | 1/1989 | New Zealand . |
| 236369 | 6/1993 | New Zealand . |
| 1464552 | 2/1977 | United Kingdom . |
| 1464553 | 2/1977 | United Kingdom . |
| 1498816 | 1/1978 | United Kingdom . |
| 1527584 | 10/1978 | United Kingdom . |

OTHER PUBLICATIONS

IVS Annual, p. 284 (Dec. 1993).
The Merck Index, Ed. 11, (1989,) Entry Nos. 201, 1091, 1733, 3888, 3904, 4050, 5647, 6390, 6890, 6891, 6985, 9217 and 9282.

Primary Examiner—Kevin E. Weddington
Attorney, Agent, or Firm—Jacobson, Price, Holman & Stern, PLLC

[57] ABSTRACT

A pour-on anthelmintic composition, including its method of preparation and use, the composition preferably having being prepared by mixing at a common temperature (I) a premix of an anthelmintic compound or compounds (for example a benzimidazole) with a transdermal vehicle (such as isopropyl myristate) with (ii) a premix of a non-ionic emulsifier with an oil capable of solubilising the emulsifier and, subsequent to the blending of the premixes (preferably after cooling), mixing the blend with a deflocculation agent/diluent or deflocculation agent/diluent mix.

37 Claims, 1 Drawing Sheet

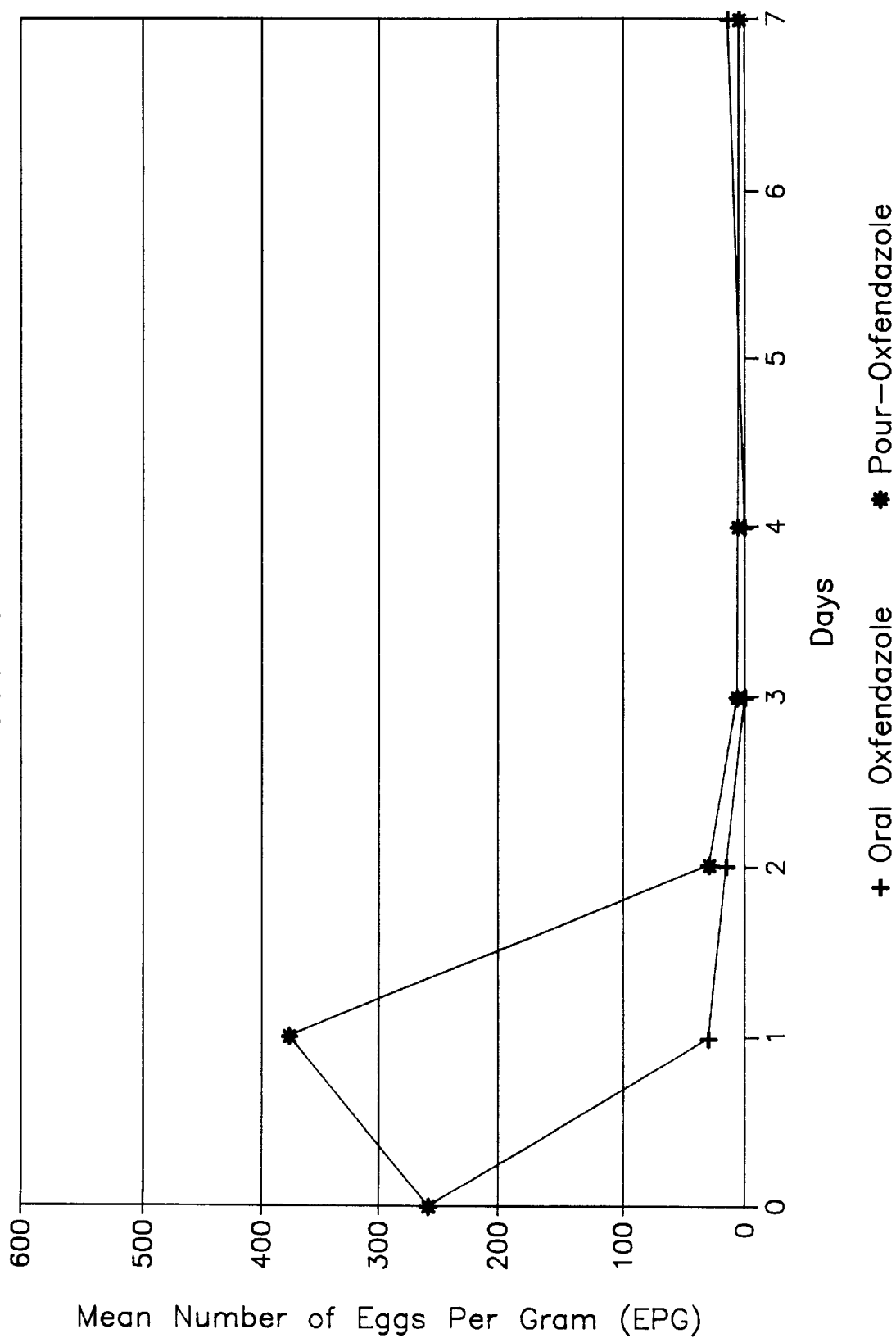

ANTHELMINTIC PREPARATION

TECHNICAL FIELD

This invention relates to a method of preparing an anthelmintic composition and/or an anthelmintic composition (including a preparation so prepared) and/or a method of using such a composition.

BACKGROUND ART

Benzimidazole anthelmintics are widely used orally in aqueous suspension formulations for the control of parasitic helminths, namely round worms (nematodes), tapeworms (cestodes), or flukes (trematode). This anthelmintic group has been used in a variety of animal species including sheep, cattle, goats, deer, horses, cats, dogs, llama buffalo and poultry. Injectable preparations of benzimidazole anthelmintics are also known. Benzimidazole anthelmintic compounds are widely used in veterinary medicine. Common forms include oxfendazole, mebendazole, fenbendazole, albendazole and the probenzimidazoles febantel and netobimin, which are metabolised to benzimidazoles within the animal.

In general, these compounds are sparingly soluble in aqueous solutions although the solubility can be improved by heating the aqueous solution.

Bayer AG British Patent Specification No. 1527584, the full content of which is hereby included by way of reference, refers to the advantages of pour-on application in veterinary practice over oral treatments and additionally discloses a pour-on formulation characterised in that the active compound is dissolved, emulsified or suspended in a suitable solvent or solvent mixture which is tolerable by the skin (optionally with addition of further auxiliaries) and applied with the aid of a suitable device, eg. measuring cup or spray bottle to the skin of the animal to be treated. The active ingredients disclosed are Tetramisole and Levamisole.

Reference should also be had to the paper "Seasonal Variation and Anthelmintic Response by Cattle to dermally applied Levamisole", B. A. Forsyth et al. Australian Veterinary Journal, Vol. 60 No.5, May 1983 and "Pharmacokinetics of ivermectin after oral or percutaneous administration to adult milking goats", E. W. Scott et al., Journal Veterinary Pharmacology, Volume 13, pages 432–435, 1990.

E. R. Squibb & Sons Inc, U.S. Pat. No. 4,145,433 discloses the option of topical or parenteral administration to mammalian hosts of benzimidazole dispersed in a non-toxic, non-pyrogenic acceptable carrier. In particular it discloses a solution for cutaneous administration being prepared by dissolving 327 mg of [5-(benzyl)sulfinyl]-1H-benzimidazole-2-yl] carbamic acid, methyl ester in a solution of about 4 cc xylene and 1 cc dimethyl sulfoxide. Such administrations are stated as being useful in treating infection caused by Haemonchus, Ostertagia, Trichostrongylus, Cooperia, Dictyocaulus, Nematodirus, Bunostomum, Strongyloides, Oesphagostomum, Trichuris and liver flukes at a recommended dosage of from 2.5–25 mg/kg body weight.

DISCLOSURE OF INVENTION

Nevertheless the sparing solubility of anthelmintics restricts their use as pour-ons.

The present invention relates to improved methods of formulating compositions of anthelmintics (preferably benzimidazoles) for topical or transdermal administration to provide a substantially stable composition despite any solubility difficulties with the (benzimidazole) active ingredient(s).

It is an object of the present invention to provide a method of preparing an alternative anthelmintic composition and/or an anthelmintic composition and/or a method of using an anthelmintic composition which will obviate or minimise the foregoing disadvantages in a simple yet effective manner or which will at least provide the public with a useful choice. More specifically, it is an object of the present invention to provide alternative veterinary preparations, and/or methods of preparation and/or of use of veterinary preparations, whereby preferably benzimidazole anthelmintics may be applied externally to animals so as to pass into and/or through the skin and into the system(s) [eg. blood, lymph and/or tissue] of the animal, providing a simple and quick administration method which is effective in achieving the necessary dose response.

In addition it may provide a simple more prolonged method of administering the anthelmintic, increasing the anthelmintics effectiveness.

Accordingly in one aspect the invention consists in a method of preparing an anthelmintic composition capable by means of dermal application of delivery of a effective anthelmintic amount one or more active ingredients into an animal systemically, said method comprising:

(i) mixing at least one anthelmintic compound with a vehicle in which said compound(s) dissolves, suspends and/or emulsifies until the vehicle/active ingredient mixture is substantially homogeneous, (ii) before, simultaneously with, or after step (i), mixing a non-ionic emulsifier with an oil capable of solubilising the non-ionic emulsifier, said mixing being at a temperature where both the non-ionic emulsifier and oil are in a liquid phase, (iii) blending the mixtures of steps (i) and (ii) at a temperature at which all components are in the liquid phase so as to provide a substantially homogeneous mixture, (iv) lowering the temperature, or allowing the lowering of the temperature, of the mixture of step (iii) while mixing (preferably so that at least said non-ionic emulsifier is no longer in the liquid phase), and (v) mixing with the suspension of step (iv) a deflocculation agent/water (or other diluent) mixture to provide the anthelmintic micro suspension preparation.

Preferably said anthelmintic active ingredient is at least one benzimidazole or prodrug therefor.

Other options include an avermectin, pyrantel, morantel, closantel, praziquantel etc.

Preferably said benzimidazole(s) or prodrug thereof is selected from the group including oxfendazole, thiabendazole, albendazole, cambenazole, fenbendazole, flubendazole, mebendazole, oxibendazole, parbendazole, thiophanate, febantel and netobimin.

Preferably said benzimidazole(s) is or are oxfendazole and/or albendazole.

Preferably said benzimidazole(s) is oxfendazole.

Preferably said vehicle is selected from the group including isopropyl myristate, dimethyl sulphoxide, diacetone alcohol, n-methyl-2-pyrrolidone, iso-propyl alcohol, dimethylforamide, and 2 pyrrolidone.

Preferably said vehicle is isopropyl myristate.

In addition to said vehicle a cosolvent and/or absorption enhancer is selected from the group including polyoxyethylen glyceroltriricinoleate, polyvinylpyrrolidone, polyoxyethylene - glycerol trihydroxystearate, dimethylformamide (DMF), dimethyl-acetamide, dimethyl isosorbide.

Preferably the mixture of step (i) is elevated in temperature prior to the blending step (iii).

Preferably the temperature of blending step (iii) is from about 55° C. to about 60° C.

Preferably the oil of step (ii) capable of solubilising the non-ionic emulsifier is a mineral oil or a vegetable oil.

Preferably said oil is selected from the group consisting of rapeseed or canola oil, polyol fatty acid ester, lauric acid hexyl, oleic acid decyl ester, 2-octyl dodecanol soybean, sunflower oil, and ground nut refined fixed oils.

Preferably said non-ionic emulsifier of step (ii) is selected from the group including sorbitan stearate, polysorbates [including ethoxy (20) sorbitan monopalmitate, ethoxy (20) sorbitan monostearate, ethoxy (4) sorbitan monostearate and ethoxy (20) sorbitan tristearate], polyoxyethylene castor oils and polyoxyethylene glycols.

Preferably said non-ionic emulsifier of step (ii) is sorbitan stearate.

Preferably the step (ii) is carried out at an elevated temperature.

Preferably said elevated temperature at which step (ii) is carried out is from about 55°C. to about 60° C.

Preferably the blending step (iii) is carried out only after the substantially homogeneous mixture of step (i) has been raised to a temperature of from about 55 ° C to about 60° C.

Preferably the temperature lowering step (iv) is to room or ambient temperature(s).

Preferably the deflocculation agent/water mixture is of a deflocculation agent selected from the group consisting of sodium lignosulphonate, silicon dioxides, poly vinyl pyrrolidones and/or said diluent is water.

Preferably said deflocculation agent is sodium lignosulphonate.

Preferably said deflocculation agent/water mixture has been mixed with a sonic mixing procedure.

Preferably said deflocculation agent/water mixture is added to the mixture of step (iv) substantially at room or ambient temperatures.

Preferably the composition comprises

| Oxfendazole | 7.5% w/v |
|---|---|
| Iso Propyl Myristate | 66.0% w/v |
| Sorbitan Stearate | 1.0% w/v |
| Sodium Lignosulphonate | 0.9% w/v |
| Canola Oil | 0.5% w/v |
| Deionised Water | Up to the 100%. |

Preferably said mixture includes at least one or more of the following compounds, a trace mineral or trace minerals, a synthetic pyrethroid or pyrethroids (eg; cypermethrin), an organic phosphate or organophosphates, closantel pyrantel morantel, praziquantel and synthetic pyrethroids.

Preferably any such optional trace mineral(s) organophosphate(s) and/or closantel sodium is mixed into (a), in the case of trace mineral(s) the pre-mix of step (iv) or (v), (b), in the case of any organophosphate(s), in a mix of step (iv) or (v), (c) in the case of closantel sodium, a mix of step (i), (d) in the case of pyrantel or morantel, a mix of step (i), (e) in the case of praziquantel a mix of step (i), (f) in the case of synthetic pyrethroid(s), a mix of step (i).

In a further aspect the invention is a benzimidazole anthelmintic composition prepared by a method as previously defined.

In still a further aspect the invention consists in an anthelmintic composition capable of being used transdermally such as by a pour-on procedure, said composition comprising at room or ambient temperature at least one benzimidazole or prodrug thereof dissolved in, suspended on and/or emulsified by a transdermal vehicle and a liquid carrier for such benzimidazole/vehicle which includes a non-ionic emulsifier, an oil which solubilises the non-ionic emulsifier, water or other suitable diluent and a deflocculation agent.

Preferably said composition comprises

| Benzimidazole(s) | 1% to 50% w/v, |
|---|---|
| Transdermal vehicle(s) | 2% to 80% w/v, |
| Non-ionic emulsifier(s) | 0.1% to 10% w/v, |
| Oil(s) | 0.1% to 10% w/v, |
| Deflocculation agent(s) | 0.1% to 10%, and |
| Water or other suitable diluent | 5% to 50% w/v. |

Preferably said benzimidazole or prodrug thereof is selected from the group consisting of oxfendazole, thiabendazole, albendazole, cambenazole, fenbendazole, flubendazole, mebendazole, oxibendazole, parbendazole, thiophanate, febantel and netobimin, said vehicle is selected from the group including isopropyl myristate, dimethyl sulphoxide, diacetone alcohol, n-methyl-2-pyrrolidone and 2 pyrrolidone, said oil is selected from the group including rapeseed or canola oil, polyol fatty acid ester, lauric acid hexyl, oleic acid decyl ester, 2-octyl dodecanol, soybean, sunflower oil, cold pressed rapeseed and ground nut refined fixed oils.

said non-ionic emulsifier is selected from the group including sorbitan stearate, polysorbates, polyoxyethylene castor oils and polyoxyethylene glycols and said deflocculation agent is selected from the group including sodium lignosulphonate, silicon dioxides, poly vinyl pyrrolidones.

Preferably said benzimidazole is oxfendazole, said vehicle is isopropyl myristate, said oil is rapeseed or canola oil said non-ionic emulsifier is sorbitan stearate and said deflocculation agent is sodium lignosulphonate.

Preferably said composition comprises

| Oxfendazole | 7.5% w/v |
|---|---|
| Iso Propyl Myristate | 66.0% w/v |
| Sorbitan Stearate | 1.0% w/v |
| Sodium Lignosulphonate | 0.9% w/v |
| Canola Oil | 0.5% w/v |
| Deionised Water | up to the 100%. |

Preferably the composition additionally includes at least one trace mineral and/or at least one organo phosphate and/or closantel sodium.

In still a further aspect the invention consists in a method of controlling helminth(s) (nematode, cestode or trematode) within an animal which comprises applying to the skin of the animal an anthelmintic composition as herein defined and thereafter allowing at least the anthelmintic compound(s) [preferably benzimidazole or prodrug compound(s)] to pass through and/or into the skin of the animal to enter the blood, lymph and/or tissue fluids of the animal in an anthelmintically effective amount.

Preferably said composition is applied by a pour-on procedure or other method of skin application.

Preferably said composition is about a 75 mg/mL suspension of oxfendazole at about a dosage rate oxfendazole/weight of animal at least twice that recommended for oral administration currently being recommended for oxfendazole anthelmintic treatment of any such animal.

Preferably said composition is about a 75 mg/mL suspension of oxfendazole at a dosage rate of about 10 mg oxfendazole/kg body weight of the animal.

Preferably the animal is a ruminant but can be other mammals or even non mammals.

Preferably said veterinary preparation also includes a surface active dispersant or wetting agent.

In a further aspect the invention consists in an anthelmintic composition capable by dermal application to an animal of delivering an anthelminticly effective amount of systemic anthelmintic active ingredient into the animal

| | |
|---|---|
| systemic anthelmintic compound(s) | 1% to 50% w/v, |
| emulsifier | 0.1% to 10% w/v, |
| carrier solvent (transdermal vehicle) | 2% to 80% w/v, |
| dispersant or wetting agent | 0.1% to 10% w/v, |
| oil | 0.1% to 10% w/v, and |
| diluent | 5% to 50% w/v. |

Preferably said anthelmintic compound is a benzimidazole.

BRIEF DESCRIPTION OF DRAWINGS

The invention also consists in methods of use thereof.

The present preferred forms of the invention will now be described. The accompanying drawing (FIG. 1) is a plot of helminth egg counts against time.

BEST MODE(S) FOR CARRYING OUT THE INVENTION

According to the invention, a veterinary preparation is provided, along with a method of preparing a veterinary preparation, and a method of using a veterinary preparation.

The preparation is so formulated as to be suitable for dermal use, e.g. spread on, spray on, or pour-on (hereinafter "pour-on"). The invention is that the benzimidazole anthelmintic is presented in a carrier or solvent (hereafter "vehicle") which is capable of being absorbed through the skin. By preference, this vehicle is iso propyl myristate, although other compounds may be substituted, for example, dimethyl sulphoxide, diacetone alcohol, N-methyl-2-pyrrolidone, 2 pyrrolidone or other suitable non-toxic compounds which can be absorbed through the skin of the target animals. Thus the formulation when applied externally to the animal will pass through the skin and into the systems of the animal where it can take effect.

A typical formulation according to the invention consists of 1% to 50% w/v benzimidazole, 2% to 80% w/v vehicle, 5% to 50% w/v diluent, 0.1% to 10% w/v non-ionic emulsifier, 0.1% to 10% w/v deflocculant and 0.1% to 10% oily component.

The emulsifier in the preferred form of the invention is sorbitan stearate but this may be substituted by other non-ionic emulsifiers, for example, polysorbates, polyoxyethylene castor oils, polyoxyethylene glycols.

The dispersant or wetting agent is in the preferred form of the invention sodium lignosulphonate, but this may be substituted by silicon dioxides, poly vinyl pyrrolidones, or other surface active agents.

The preparation also contains an oily component. In the most presently preferred form of the invention, this is rapeseed oil but this may be substituted by polyol fatty acid ester, lauric acid hexyl, oleic acid decyl ester, 2-octyl dodecanol or other vegetable oils such as soybean or sunflower oil.

The preparation is made up to volume with a diluent, such as deionised water. This diluent may be substituted by or include or be (any one or more) other miscible diluents such as propylene glycol, sorbitol or glycerol.

EXAMPLE

| | |
|---|---|
| Oxfendazole | 7.5% w/v |
| Iso Propyl Myristate | 66.0% w/v |
| Sorbitan Stearate | 1.0% w/v |
| Sodium Lignosulphonate | 0.9% w/v |
| Rapeseed Oil | 0.5% w/v |
| Deionised Water | Up to the 100%. |

Other, anthelmintic or therapeutic substances may also be included in the preparation if desired, for example, minerals, trace elements, synthetic pyrethroids and organophosphates.

The composition of the present may be prepared as follows:

The benzimidazole anthelmintic, for example oxfendazole, is added to the carrier solvent, for example iso propyl myristate, and the two compounds are mixed until the mixture is thoroughly wetted.

The non-ionic emulsifier, for example sorbitan stearate is then added to the mixture while maintaining stirring, followed, while continuing to stir, by the dispersant or wetting agent, for example sodium lignosulphonate, and the suitable oily component, for example rapeseed or canola oil. The mixture is then made up to volume with the diluent, for example deionised water. The total mixture is then continued to be mixed until it is substantially homogeneous.

The more preferred procedure is (i) mixing at least one anthelmintic compound (eg: oxfendazole) with a vehicle (eg: isopropyl myristate) in which said compound(s) dissolves, suspends and/or emulsifies until the vehicle/active ingredient mixture is substantially homogeneous, (ii) before, simultaneously with, or after step (i), mixing a non-ionic emulsifier (eg: sorbitan stearate) with an oil (eg: rapeseed oil) capable of solubilising the non-ionic emulsifier, said mixing being at a temperature (preferably elevated to 55° C. to 60° C.) where both the non-ionic emulsifier and oil are in a liquid phase, (iii) blending the mixtures of steps (i) and (ii) at a temperature (preferably elevated to 55° C. to 60° C.) at which all components are in the liquid phase so as to provide a substantially homogeneous mixture, (iv) lowering the temperature, or allowing the lowering of the temperature, of the mixture of step (iii) (eg: to room or ambient temperature) while mixing so that at least said non-ionic emulsifier is no longer in the liquid phase, and (v) mixing with the suspension of step (iv) a defloculation agent/diluent mixture (eg: sodium lignosulphate/water) to provide the anthelmintic micro suspension preparation, said diluent being selected from the group comprising water, propylene glycol sorbitol and glycerol.

This procedure provides an anthelmintic composition which over time can provide most effective helminth control.

The following eleven formulations give examples of different formulations within the present invention.

FORMULATION 1

| | |
|---|---|
| Oxfendazole | 7.5% w/v |
| Iso Propyl Myristate | 66.0% w/v |

| | |
|---|---|
| Canola Oil | 0.5% w/v |
| Liposorb S | 1.0% w/v |
| Sodium Lignosulphonate | 0.9% w/v |
| Benzyl Alcohol | 5.0% w/v |
| Deionised Water | qs to 100% v/v |

FORMULATION 2

| | |
|---|---|
| Albendazole | 7.5% w/v |
| Iso Propyl Myristate | 66.0% w/v |
| Canola Oil | 0.5% w/v |
| Liposorb S | 1.0% w/v |
| Sodium Lignosulphonate | 0.9% w/v |
| Benzyl Alcohol | 5.0% w/v |
| Deionised Water | qs to 100% v/v |

FORMULATION 3

| | |
|---|---|
| Fenbendazole | 2.5%–10% w/v |
| Iso Propyl Myristate | 66.0% w/v |
| Canola Oil | 0.5% w/v |
| Liposorb S | 1.0% w/v |
| Sodium Lignosulphonate | 0.9% w/v |
| Benzyl Alcohol | 5.0% w/v |
| Deionised Water | qs to 100% v/v |

FORMULATION 4

| | |
|---|---|
| Oxfendazole | 7.5% w/v |
| Closantel - Sodium | 2.5% w/v–5.0% w/v |
| Iso Propyl Myristate | 66.0% w/v |
| Canola Oil | 0.5% w/v |
| Liposorb S | 1.0% w/v |
| Sodium Lignosulphonate | 0.9% w/v |
| Benzyl Alcohol | 5.0% w/v |
| Deionised Water | qs to 100% v/v |

FORMULATION 5

| | |
|---|---|
| Praziquantel | 2.5% w/v |
| Oxfendazole | 7.5% w/v |
| Iso Propyl Myristate | 66.0% w/v |
| Canola Oil | 0.5% w/v |
| Sodium Lignosulphonate | 0.9% w/v |
| Liposorb S | 1.0% w/v |
| Benzyl Alcohol | 5.0% w/v |
| Deionised Water | qs to 100% v/v |

FORMULATION 6

| | |
|---|---|
| Oxfendazole | 7.5% w/v |
| Cypermethrin | 2.5% w/v |
| Iso Propyl Myristate | 66.0% w/v |
| Canola Oil | 0.5% w/v |
| Sodium Lignosulphonate | 0.9% w/v |
| Benzyl Alcohol | 5.0% w/v |
| Liposorb S | 1.0% w/v |
| Deionised Water | qs to 100% v/v |

FORMULATION 7

| | |
|---|---|
| Oxfendazole | 7.5% w/v |
| Iso Propyl Myristate | 66.0% w/v |
| Canola Oil | 0.5% w/v |
| Sodium Lignosulphonate | 0.9% w/v |
| Benzyl Alcohol | 5.0% w/v |
| Liposorb S | 1.0% w/v |
| Copper Disodium Ethylenediamine Tetra Acetate | 10.7% w/v |
| Zinc EDTA | 5.4% w/v |
| Cobalt EDTA | 1.1% w/v |
| Sodium Selenate | 0.57% w/v |
| EDDI | 0.57% w/v |
| Deionised Water | qs to 100% v/v |

FORMULATION 8

| | |
|---|---|
| Benzimidazole(s) | 1%–20% w/v |
| Transdermal Vehicle(s) | 2%–80% w/v |
| Non-ionic Emulsifier(s) | 0.1%–10% w/v |
| Oil(s) | 0.1%–10% w/v |
| Deflocculation Agent(s) | 0.1%–10% w/v |
| Preservative(s) | 0.5%–10% w/v |
| Water or suitable diluent | 1%–50% v/v |

FORMULATION 9

| | |
|---|---|
| Benzimidazole(s) | 1%–20% w/v |
| Anthelmintic(s) | 1%–5% w/v |
| Transdermal Vehicle(s) | 2%–80% w/v |
| Non-ionic Emulsifier(s) | 0.1%–10% w/v |
| Oil(s) | 0.1%–10% w/v |
| Deflocculation Agent(s) | 0.1%–10% w/v |
| Preservative(s) | 0.5%–10% w/v |
| Water or other suitable diluent | 1%–50% v/v |

FORMULATION 10

| | |
|---|---|
| Benzimidazole(s) | 1%–20% w/v |
| Pyrethroid(s) | 1%–5% w/v |
| Transdermal Vehicle(s) | 2%–80% w/v |
| Non-ionic Emulsifier(s) | 0.1%–10% w/v |
| Oil(s) | 0.1%–10% w/v |
| Deflocculation Agent(s) | 0.1%–10% w/v |
| Preservative(s) | 0.5%–10% w/v |
| Water or other suitable diluent | 1%–50% v/v |

FORMULATION 11

| | |
|---|---|
| Anthelmintic(s) (including Benzimidazole(s)) | 1%–20% w/v |
| Transdermal Vehicle(s) | 2%–80% w/v |
| Non-ionic Emulsifier(s) | 0.1%–10% w/v |
| Oil(s) | 0.1%–10% w/v |
| Deflocculation Agent(s) | 0.1%–10% w/v |
| Trace Mineral(s) | 1%–25% w/v |
| Preservative(s) | 0.5%–10% w/v |
| Water or other suitable diluent | 1%–50% v/v |

This formulation may be administered to cattle, for example, in volume dosages of 35–45 mls for cattle of 250–310 kg body weight. Of course veterinary advice should also be sought regarding dosages. Dosages in similar ratios are applicable to other animals, eg: sheep, goats, horses, deer, cats, dogs, camel, llama and buffalo.

Thus it can be seen that an improved benzimidazole anthelmintic preparation, a method of preparing a veterinary preparation, and a method of using a veterinary preparation are provided by the invention in its preferred form which have the advantage of increasing the convenience and effectiveness of use of such compounds, through providing for efficacious dermal application.

Thus the formulation when applied externally will pass into and/or through the skin and be transported by the blood, lymph or tissue fluids to act on the helminth (nematode, cestode or trematode) both within body tissues and body organs including muscle, lung, liver and kidney and within the lumen of both the gastrointestinal and respiratory tract.

The mechanism of action of the benzimidazole anthelmintics on helminths is believed to be due to their disruption of intracellular microtubular transport systems by binding selectively to and damage of, helminth tubulin, preventing tubulin polymerisation and the inhibition of microtubule formation. Benzimidazoles have also been shown to act at higher levels as inhibitors of metabolic enzymes, including malate dehydrogenase and fumarate reductase, and disrupt metabolic pathways within the helminth. Orally Benzimadazoles appear to be most effective as anthelmintics (drenches) when given over several days rather than as an oral single dose.

The preparation may be applied may be applied according to the invention, dermally, eg. as a pour-on on to the mid line of the back or neck of animals such as cattle. The active ingredient (ie. the anthelmintic) is absorbed through the skin and into the blood, tissues and tissue fluids of the animal.

Data based on the application of the said pour on, in this case oxfendazole, at 2.2 times the oral dose rate (ie. 10 mg/kg) produced blood serum levels up to 0.2 $\mu$g/mL which is comparable with the blood levels seen in calves orally administered with oxfendazole at a dose rate of 4.5 mg/kg. Blood oxfendazole levels in the said pour on calves were generally lower and unexpectedly persistent, with low levels of oxfendazole detected in their blood at day 3 and 4 after administration. Blood levels in calves that received oral oxfendazole were below detection (0.025 μg/mL) at day 3.

A slower action was also seen in the reduction of faecal egg counts in the pour on group with significant reductions on day 2 and 3 after treatment compared with a significant reduction occurring at day 1 and 2 in the oral group (see FIG. 1).

FIG. 1 shows Faecal Egg Counts (F.E.C's) in Eggs per gram (EPG) in 6 month old Friesan Calves, treated with oral oxfendazole (Synanthic'™) at a dose rate of 4.5 mg per kg, the trial oxfendazole pour-on at 10.0 mg/kg and untreated control animals. Treatment was at day 0.

The pour-on formulation used for these FEC/Time trials was

| | |
|---|---|
| Oxfendazole | 7.5% w/v |
| Iso Propyl Myristate | 66.0% w/v |
| Sorbitan Stearate | 1.0% w/v |
| Sodium Lignosulphonate | 0.9% w/v |
| Canola Oil | 0.5% w/v |
| Deionised Water | Up to the 100%. |

It has already been demonstrated that treatment regimes that provide more prolonged levels of benzimidazoles over a number of days such as appear to be demonstrated in this pour on product, increases the effectiveness of the anthelmintic.

Table 1 is a comparison of Faecal Egg Counts (F.e.c's) in 6 Month Old Friesan Calves Treated with Oral Oxfendazole (Synanthic™) At 4.5 Mg/Kg and Trial Pour Oxfendazole Product At 13.5 Mg/kg.

TABLE 1

Oxfendazole Pour-on

| Animal No | Treatment Group | Day 1 | Day 0 | mean: -1,0 | Day 7 | Day 14 |
|---|---|---|---|---|---|---|
| 2 | Control | — | 0 | 0 | 0 | 100 |
| 5 | Control | 50 | 100 | 75 | 0 | 0 |
| 10 | Control | 100 | 200 | 150 | 100 | 300 |
| 12 | Control | 50 | 50 | 50 | 100 | 50 |
| 25 | Control | 500 | 300 | 400 | 200 | 400 |
| 33 | Control | 500 | 150 | 325 | 0 | 0 |
| 51 | Control | 200 | 0 | 100 | 450 | 300 |
| 58 | Control | 50 | 0 | 25 | 200 | 150 |
| 59 | Control | 450 | 400 | 425 | 400 | 600 |
| 70 | Control | 50 | 150 | 100 | 100 | N.D. |
| geometric means | | 217 | 135 | 165 | 150 | 211 |
| 1 | Oral | 50 | 100 | 75 | 0 | 0 |
| 3 | Oral | 200 | 200 | 200 | 50 | 0 |
| 6 | Oral | 50 | 200 | 125 | 50 | 0 |
| 8 | Oral | 50 | 50 | 50 | 0 | 0 |
| 11 | Oral | 350 | 50 | 200 | 0 | 0 |
| 13 | Oral | 50 | 50 | 50 | 0 | 0 |
| 16 | Oral | 350 | 100 | 225 | 0 | 0 |
| 30 | Oral | 300 | 250 | 275 | 0 | 50 |
| 36 | Oral | 200 | 300 | 250 | 50 | 0 |
| 38 | Oral | 100 | 50 | 75 | 0 | 0 |
| 41 | Oral | 300 | 200 | 250 | 0 | 0 |
| 45 | Oral | 100 | 0 | 50 | 0 | 0 |
| 47 | Oral | 500 | 300 | 400 | 0 | 0 |
| 55 | Oral | 50 | 150 | 100 | 0 | 0 |
| 61 | Oral | 350 | 500 | 425 | 50 | 50 |
| 62 | Oral | 300 | 50 | 175 | 0 | 0 |
| 66 | Oral | 50 | 50 | 50 | 0 | 0 |
| 73 | Oral | 50 | 0 | 25 | 0 | 0 |
| 74 | Oral | 400 | 0 | 200 | 0 | 50 |
| geometric mean | | 190 | 139 | 168 | 10 | 8 |

TABLE 1-continued

Oxfendazole Pour-on

| Animal No | Treatment Group | Day 1 | Day 0 | mean: -1,0 | Day 7 | Day 14 |
|---|---|---|---|---|---|---|
| 4 | Pour-on | 50 | 0 | 25 | 0 | 0 |
| 7 | Pour-on | 230 | 0 | 125 | 0 | 0 |
| 9 | Pour-on | 150 | — | 75 | 0 | 0 |
| 14 | Pour-on | 100 | 100 | 100 | 0 | 0 |
| 18 | Pour-on | 150 | 100 | 125 | 0 | 0 |
| 20 | Pour-on | 50 | 0 | 25 | 0 | 0 |
| 21 | Pour-on | 100 | 250 | 175 | 0 | 50 |
| 22 | Pour-on | 100 | 100 | 100 | 0 | 0 |
| 23 | Pour-on | 50 | 100 | 75 | 0 | 0 |
| 26 | Pour-on | 50 | 0 | 25 | 0 | 0 |
| 28 | Pour-on | 350 | 500 | 425 | 0 | 0 |
| 31 | Pour-on | 850 | 400 | 625 | 0 | 0 |
| 37 | Pour-on | 100 | 50 | 75 | 0 | 0 |
| 40 | Pour-on | 150 | 350 | 250 | 0 | 0 |
| 42 | Pour-on | 150 | 150 | 150 | 0 | 50 |
| 44 | Pour-on | 400 | 0 | 200 | 0 | 0 |
| 50 | Pour-on | 900 | 1550 | 1225 | 200 | 750 |
| 57 | Pour-on | 50 | 0 | 25 | 0 | 0 |
| 60 | Pour-on | 50 | 50 | 50 | 0 | 0 |
| 76 | Pour-on | 50 | 0 | 25 | 0 | 0 |
| geometric mean | | 205 | 195 | 195 | 10 | 42 |

SUMMARY

Comparison of oral and pour-on formulations. Treatment groups are: Group 0=untreated controls, Group 1=oral drench, and Group 3=pour-on formulation Note: All analyses were carried out on log-transformed FEC's.

The analysis of faecal egg counts (FEC's) shows that there were no significant differences between any of the groups either on day −1 or day 0. Subsequently, on days 7, 14 and 21 post-treatment there was a high significant difference between the untreated control group and the groups treated with oxfendazole ($p<0.0001$). There were no significant differences between the orally or topically treated groups.

We claim:

1. A method of preparing a composition of a benzimidazole anthelmintic compound or pro-drug thereof which is effective by dermal application to a mammal of delivery of the benzimidazole compound or pro-drug thereof systemically into the mammal to elicit an anthelmintic response, said method comprising:

(i) mixing at least one anthelmintic benzimidazole compound or pro-drug thereof with an organic transdermal vehicle into which said benzimidazole compound or pro-drug thereof substantially dissolves, suspends and/or emulsifies, said benzimidazole compound or pro-drug thereof being substantially insoluble in water and being a solid at room or temperate ambient temperatures;

(ii) before, simultaneously with, or after step (i), mixing an organic non-ionic emulsifier with an oil capable of solubilizing the non-ionic emulsifier at least above room or temperate ambient temperatures, said mixture being at a temperature or temperatures where both the non-ionic emulsifier and the oil are in a liquid phase;

(iii) blending the mixtures of steps (i) and (ii) at a temperature or temperatures at which the organic transdermal vehicle, the oil and the organic non-ionic emulsifier are in the liquid phase so as to provide a substantially homogeneous organic phase mixture which includes, in particulate form, the benzimidazole compound or pro-drug thereof;

(iv) lowering the temperature, or allowing the lowering of the temperature, of the organic phase mixture of (iii) while mixing so that at least said non-ionic emulsifier in addition to said benzimidazole compound or pro-drug thereof is no longer in the liquid phase, and (v) mixing with the suspension of step (iv) a deflocculation agent/diluent mixture to provide a micro suspension, said diluent being selected from water, propylene glycol, sorbitol and glycol but with the proviso that water is selected.

2. A method of claim 1 wherein said benzimidazole(s) or pro-drug thereof is or are selected from the group consisting of oxfendazole, thiabendazole, albendazole, cambendazole, fenbendazole, flubendazole, mebendazole, oxibendazole, parbendazole, thiophanate, febantel and netobimin.

3. A method as claimed in claim 2 wherein said benzimidazole(s) is oxfendazole.

4. A method as claimed in claim 1 wherein said organic transdermal vehicle is selected from the group consisting of isopropyl myristate, dimethyl sulphoxide, diacetone alcohol n-methyl-2-pyrrolidone, dimethyl formamide and 2-pyrrolidone.

5. A method as claimed in claim 4 wherein said organic transdermal vehicle is isopropyl myristate.

6. A method as claimed in claim 1 wherein the temperature of the mixture of step (i) is elevated prior to the blending step (iii).

7. A method as claimed in claim 6 wherein the temperature of the blending step (iii) is from 55° C. to 60° C.

8. A method as claimed in claim 1 wherein the oil of step (ii) is a mineral oil or a vegetable oil.

9. A method as claimed in claim 8 wherein said oil is selected from the group consisting of canola oil, rapeseed oil, polyol fatty acid ester, lauric acid hexyl ester, oleic acid decyl ester, 2-octyl dodecanol, soybean and sunflower oil.

10. A method as claimed in claim 1 wherein said non-ionic emulsifier of step (ii) is selected from the group consisting of sorbitan stearate, polysorbates, polyoxyethylene castor oils and polyoxyethylene glycols.

11. A method as claimed in claim 10 wherein said non-ionic emulsifier of step (ii) is sorbitan stearate.

12. A method as claimed in claim 1 wherein the step (ii) is carried out at an elevated temperature.

13. A method as claimed in claim 12 wherein said elevated temperature at which step (ii) is carried out is from 55° C. to 60° C.

14. A method as claimed in claim 1 wherein the blending step (iii) is carried out only after the substantially homogeneous mixture of step (i) has been raised to a temperature of from 55° C. to 60° C.

15. A method as claimed in claim 1 wherein the temperature lowering step (iv) is to room or temperate ambient temperature(s).

16. A method as claimed in claim 1 wherein the deflocculation agent is selected from the group consisting of sodium lignosulphonate, silicon dioxides, poly vinyl pyrrolidones and said diluent is water.

17. A method as claimed in claim 16 wherein said deflocculation agent is sodium lignosulphonate.

18. A method as claimed in claim 16 wherein said deflocculation agent/water mixture has been mixed with a sonic mixing procedure.

19. A method as claimed in claim 18 wherein said deflocculation agent/water mixture is added to the mixture of step (iv) substantially at room or temperate ambient temperature(s).

20. A method as claimed in claim 1 wherein the composition comprises:

| | |
|---|---|
| Oxfendazone | 7.5% w/v |
| Iso Propyl Myristate | 66.0% w/v |
| Sorbitan Stearate | 1.0% w/v |
| Sodium Lignosulphonate | 0.9% w/v |
| Canola Oil | 0.5% w/v |
| Deionized Water | Up to the 100%. |

21. A method as claimed in claim 1 wherein said composition further comprises at least one compound selected from the group consisting of a trace mineral or trace minerals, synthetic pyrethroid or pyrethroids, an organic phosphate or organo phosphate and closantel sodium.

22. A method as claimed in claim 21 wherein said trace mineral(s), organo phosphate(s) and/or closantel sodium is mixed into
(a) in the case of trace mineral(s) the premix of step (iv) or (v);
(b) in the case of any organic phosphate(s), in a mix of step (iv) or (v);
(c) in the case of closantel sodium, a mix of step (i);
(d) in the case of pyrantel or morantel, a mix of step (i);
(e) in the case of praziquantel, a mix of step (i); and
(f) in the case of synthetic pyrethroid(s), a mix of step (i).

23. A method as claimed in claim 10 wherein the non-ionic emulsifier of step (ii) is ethoxy (20) sorbitan monopalmitate, ethoxy (20) sorbitan monostearate, ethoxy (4) sorbitan monostearate or ethoxy (20) sorbitan tristearate.

24. An anthelmintic composition prepared by a method as claimed in claim 1.

25. An anthelmintic composition capable of being applied by a pour-on procedure to an animal to deliver a systemically effective anthelmintic amount of the active ingredient benzimidazole or pro-drug thereof, said composition comprising at room or temperate ambient temperature(s) at least one benzimidazole or pro-drug thereof dissolved in, suspended in and/or emulsified by an organic transdermal vehicle and a liquid carrier for such benzimidazole or pro-drug thereof/vehicle which comprises a non-ionic emulsifier, an oil which can solubilize the non-ionic emulsifier at elevated temperatures, water, and a deflocculation agent.

26. A composition as claimed in claim 25 comprising:

| | |
|---|---|
| Benzimidazole(s) | 1% to 50% w/v |
| Transdermal vehicle(s) | 2% to 80% w/v |
| Non-ionic emulsifier(s) | 0.1% to 10% w/v |
| Oil(s) | 0.1 to 10% w/v |
| Deflocculation agent(s) | 0.1 to 10% w/v |
| Water or other suitable diluent | 5% to 50% w/v. |

27. A composition as claimed in claim 25 wherein said benzimidazole or pro-drug thereof is selected from the group consisting of oxfendazole, thiabendazole, albendazole, cambendazole, fenbendazole, flubendazole, mebendazole, oxibendazole, parbendazole, thiophanate, febantel, and netobimin,
said vehicle is selected from the group consisting of isopropyl myristate, dimethyl sulphoxide, diacetone alcohol, n-methyl-2-pyrrolidone, and 2-pyrrolidone,
said oil is selected from the group consisting of canola oil, polyol fatty acid ester, lauric acid hexyl ester, oleic acid decyl ester, 2-octyl dodecanol, soybean and sunflower oil, rapeseed, and ground nut refined fixed oils, said non-ionic emulsifier is selected from the group consisting of sorbitan stearate, polysorbates, polyoxyethylene castor oils and polyoxyethylene glycols and said deflocculation agent is selected from the group consisting of sodium lignosulphonate, silicon dioxides polyvinyl pyrrolidones.

28. A composition as claimed in claim 25 wherein said benzimidazole is oxfendazole, said vehicle is isopropyl myristate, said oil is canola oil, said non-ionic emulsifier is sorbitan stearate and said deflocculation agent is sodium lignosulphonate.

29. A composition as claimed in claim 25 which comprises:

| | |
|---|---|
| Oxfendazole | 7.5% w/v |
| Iso Propyl Myristate | 66.0% w/v |
| Sorbitan Stearate | 1.0% w/v |
| Sodium Lignosulphonate | 0.9% w/v |
| Canola Oil | 0.5% w/v |
| Deionized Water | Up to the 100%. |

30. A composition as claimed in claim 25 which further comprises at least one trace mineral and/or at least one organo phosphate and/or closantel sodium and/or praziquantel and/or pyrantel, and/or morantel, and/or synthetic pyrethroids.

31. A composition of claim 27 wherein the non-ionic emulsifier is ethoxy (20) sorbitan monopalmitate, ethoxy (20) sorbitan monostearate, ethoxy (4) sorbitan monostearate or ethoxy (20) sorbitan tristearate.

32. An anthelmintic composition capable by dermal application to an animal of delivering an anthelmintically effective amount of a benzimidazole or pro-drug thereof into the animal which comprises:

| | |
|---|---|
| at least one benzimidazole or pro-drug thereof | 1% to 50% w/v; |
| a non-ionic emulsifier | 0.1% to 10% w/v; |
| an organic transdermal vehicle | 2% to 80% w/v; |
| a dispersant or wetting agent | 0.1 to 10% w/v; |
| an oil suitable for solubilizing the non-ionic emulsifier | 0.1% to 10% w/v; and |
| water | 5% to 50% w/v. |

33. A method of controlling helminth(s) within a non-human animal which comprises applying to the skin of the animal a composition as claimed in claim 25 and thereafter allowing at least the active anthelmintic compound(s) to pass through and/or into the skin of the animal to enter the blood, lymph and/or tissue fluids of the animal in an anthelmintically effective amount.

34. A method as claimed in claim 33 wherein said composition is applied by a pour-on procedure.

35. A method as claimed in claim 34 wherein said composition is about a 75 mg/mL suspension of oxfendazole applied at about a dosage rate oxfendazole/weight of the animal of at least twice the oral administration dosage were oxfendazole orally administered as an anthelmintic treatment of such an animal.

36. A method as claimed in claim 34 wherein said composition is about a 75 mg/mL suspension of oxfendazole applied at a dosage rate of about 10 mg oxfendazole/kg body weight of the animal.

37. A method as claimed in claim 33 wherein the animal is a ruminant.

\* \* \* \* \*